United States Patent [19]
Lim et al.

[11] Patent Number: 5,670,698
[45] Date of Patent: Sep. 23, 1997

[54] SYNTHESIS OF 1-ACETOXY-2-METHYLNAPHTHALENE

[75] Inventors: Mu-Ill Lim, Trumbull; Yuh-Guo Pan, Stamford; Linas Stasaitis, Fairfield; James Anderson, Bethel, all of Conn.

[73] Assignee: Bristol-Myers Squibb Company, New York, N.Y.

[21] Appl. No.: 699,259

[22] Filed: Aug. 19, 1996

[51] Int. Cl.$^6$ ............................................. C07C 69/00
[52] U.S. Cl. ................................................... 560/139
[58] Field of Search ..................................... 560/139

[56] References Cited

U.S. PATENT DOCUMENTS

| | | | |
|---|---|---|---|
| 3,649,675 | 3/1972 | Koehl | 260/488 |
| 5,200,116 | 4/1993 | Heller | 252/586 |
| 5,529,583 | 6/1996 | Lim et al. | 8/408 |

*Primary Examiner*—Samuel Barts
*Attorney, Agent, or Firm*—Morton S. Simon

[57] ABSTRACT

A one pot process is provided in which a Mannich base of the formula 5 is reacted with acetic anhydride to produce a diacetate derivative. Without any intermediate isolation, the derivative is hydrogenated to produce a reaction mixture containing 1-acetoxy-2-methylnaphthalene which is readily precipitated from the reaction mixture by addition of water.

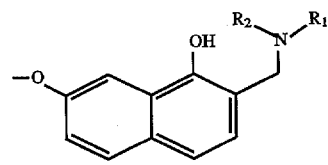

8 Claims, No Drawings

SYNTHESIS OF 1-ACETOXY-2-METHYLNAPHTHALENE

The present invention relates to a process for the synthesis of 1-acetoxy-2-methylnaphthalene (1) or 1-naphthalenol-2-methylacetate. The instant invention provides an efficient and inexpensive method for producing 1-acetoxy-2-methyl naphthalene from 2-piperidinomethyl-1-naphthol. Two-step transformations, which include acetylation and reduction, are carried out in a one-pot operation.

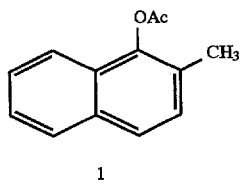

1

BACKGROUND OF THE INVENTION

U.S. Pat. No. 5,344,463 discloses hair dye compositions and a method utilizing 2-methyl-1-naphthol as a coupler. However, 2-methyl-1-naphthol decomposes upon standing at room temperature. Within several weeks, it changes from a white crystalline compound to a dark liquid. This makes it very difficult to handle and store. When incorporated in an alkaline formulation, 1-acetoxy-2-methylnaphthalene (1) gradually generates 2-methyl-1-naphthol. Consequently, it can serve as a storage stable form of 2-methyl-1-naphthol. There is, however, no economical process known to the art for producing 1-acetoxy-2-methylnaphthalene (1). The present invention provides a simple and inexpensive process for producing such compound.

DISCUSSION OF THE PRIOR ART

Kowalski, J.; Ploszynska J.; Electrochimica Acta, 1990, 35, 1739 disclose the electrochemical acetoxylation of 2-methylnaphthalene to 1-acetoxy-2-methylnaphthalene in a yield of 32.8%. The reaction is disadvantageous in that it requires a high degree of dilution. 2-Methylnaphthalene (49.8 mg) is dissolved in 150 ml acetic acid. The necessity of a high degree of dilution makes the process impractical to use for the preparation of large quantities of 1-acetoxy-2-methylnapthalene.

Baciocchi, E.; Rol, C.; and Sebastiani, G. V.; J. Chem. Research (S), 1983, 232, disclose a product and kinetic study of the oxidation of selected aromatic compounds by cerium (IV) acetate. 2-Methylnaphthalene (4.1 mmoles) and Ce(OAc)$_4$ (4.1 mmoles) were mixed in 50 ml of acetic acid under a nitrogen blanket and in the dark. The oxidation reaction was carried out under heterogeneous conditions due to the low stability of Ce(OAc)$_4$. Yields of 1-acetoxy-2-methylnaphthalene ranged from 7 to 17% depending on the reaction time and temperature. The above reaction is disadvantageous in that it must be carried out under a nitrogen blanket and in the dark. Moreover, it affords a low yield.

Baciocchi, E.; Rol, C.; and Sebastiani, G. V.; Gazzetta Chimica Italiana, 1982, 513, disclose competition between nuclear and side chain substitution in the oxidation of alkyl aromatic compounds by cerium (IV) ammonium nitrate and cobalt (III) acetate. A mixture of 4 mmoles of 2-methylnaphthalene and 4 mmoles of ceric ammonium nitrate in 250 ml acetic acid was stirred for 1.5 hours. The reaction mixture was poured into water and extracted with ethyl ether. The organic layer was washed with sodium bicarbonate solution, dried over sodium sulfate, evaporated and analyzed. Even though the overall conversion is 60–70%, the process is disadvantageous in that it gives four reaction products in respective ratios of 31.8 (1) : 10.7 : 3.9 : 1. If cobalt triacetate is employed instead of ceric ammonium nitrate, five reaction products are produced in a respective ratio of 4 : 8 : 4 : 1 : 33 (1). Moreover, whether ceric ammonium nitrate or cobalt acetate is employed, a disadvantageous separation step is required in order to obtain the desired 1-acetoxy-2-methylnaphthalene.

Research Disclosure, January 1975, 27, concerns incorporated dye-forming blocked developers. In accordance with the process disclosed, a mixture of 65.7 g (0.37 mole) of 2-morpholinomethyl-1-naphthol, 15 g of 10% Pd/C, and 540 ml of ethanol was hydrogenated at ambient temperature and at an initial pressure of 62 psi. The theoretical amount of hydrogen was absorbed in approximately one hour. The catalyst was removed by filtration and the filtrate was concentrated under vacuum. The residue was taken up in ether, extracted with 10% hydrochloric acid then with saturated aqueous NaCl, dried over anhydrous sodium sulfate, then concentrated under vacuum to yield 37.9 g 2-methyl-1-naphthol (65% yield). The acetate (1) was prepared in a yield of 61% using acetic anhydride-pyridine. The overall yield was 40%. This prior art process is disadvantageous in that the intermediate compound, 2-morpholinomethyl-1-naphthol, does not precipitate from water, thus an extraction step is required. Moreover, high loading (20%) of 10% Pd/C is required. Still further, both an extraction step and acetylation step are necessary. Thus, the entire process disadvantageously requires three steps.

Muthyala, R.; Katritzky, A. P.; Lan, X.; Dyes and Pigments, 1994, 25, 303 disclose a reaction wherein a mixture of (2-benzotriazole-1-yl-methyl)-1-naphthol and lithium aluminum hydride in tetrahydrofuran was heated under reflux for 24 hours. After flash column chromatography, 2-methyl-1-naphthol was obtained in a yield of 70%. The 2,2'-dimer was also produced. This prior art process is disadvantageous in that it introduces a benzotriazole ring which must be removed by reduction with lithium aluminum hydride in tetrahydrofuran. This reaction requires anhydrous conditions. 2-Methyl-1-naphthol is isolated by column chromatography. The process requires a separate acetylation step and is not economical.

Shen, A. Y.; Hwang, M. H.; Roffler, S.; Chan, C. F.; Arch. Pharm. 1995, 328, 197 describe the synthesis of 2-hydroxymethyl-1-naphthol diacetate. The compound was obtained in 35% yield by treatment of 2-morpholinomethyl-1-naphthol with acetic anhydride. The yield was very low. Consequently, the process is not economical.

U.S. Pat. No. 5,420,362 discloses a synthesis for the production of 2-methyl-1-naphthol. 4-Chloro-1-naphthol is reacted with a secondary amine and formaldehyde to produce a reaction mixture containing a Mannich base which is hydrogenated to produce 2-methyl-1-naphthol. The process of this patent is disadvantageous in that it involves the use of a very expensive starting material, 4-chloro-1-naphthol, and is not economical for large scale use.

Our pending U.S. patent application Ser. No. 08-527,911 describes the synthesis of 1-acetoxy-2-methylnaphthalene by the reaction of 2-methyl-1-naphthol with acetic anhydride in the presence of triethylamine. The process of this patent employs the isolated 2-methyl-1-naphthol for the synthesis. The starting material is expensive to prepare and consequently the process of this published application is disadvantageous.

Yarboro, T. L.; Karr, C.; J. Org. Chem. 1959, 24, 1141 disclose a process wherein 1-bromo-2-methyl naphthalene is convened into 2-methyl-1-naphthalene boronic acid via Grignard reaction. The boronic acid is oxidized by 30% hydrogen peroxide to produce 2-methyl-1-naphthol in 51% yield. This prior art process is disadvantageous in that it involves 4 steps and is not economical.

Nagata, W.; Okada, K.; Aoki, T.; Synthesis, 1979, 365 disclose preparation of 2-hydroxymethyl-1-naphthol by reaction of 1-naphthol with formaldehyde and benzeneboronic acid followed by oxidation with hydrogen peroxide. The 2-hydroxymethyl-1-naphthol thus prepared was characterized as the diacetate. This prior art process uses benzeneboronic acid, an expensive material. Moreovever, extraction steps are required. Therefore, the process is not economical.

The present inventors investigated a method based on the process disclosed in the 1975 Research Disclosure article previously discussed. 1-Acetoxy-2-methylnaphthalene was synthesized via piperidinomethyl Mannich base and hydrogenation followed by acetylation. This is illustrated by the reaction scheme and Example 1, which follow:

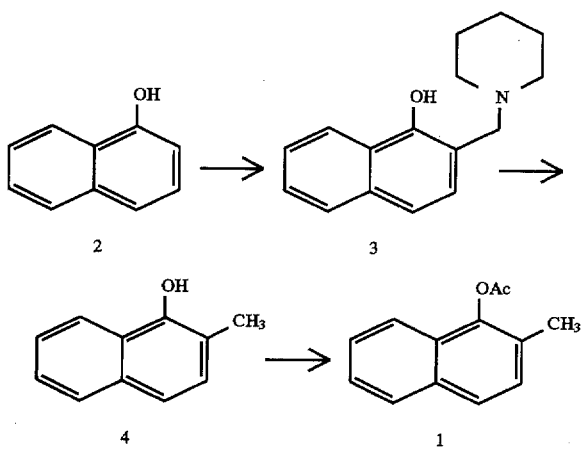

EXAMPLE 1

Synthesis of 1-acetoxy-2-methyl naphthalene Via piperidinomethyl-1-naphthol

To a solution of 288.4 g (2 moles) of 1-naphthol (1) in 1.5 liters ethanol in an ice bath, 200.4 g (2.46 moles) of formaldehyde (37 wt % in water) were added, followed by 204.4 g (2.4 moles) piperidine. The reaction mixture was stirred for one hour, then poured over 2.5 liters of a slurry of ice and water. The resulting precipitate was collected and washed with cold water three times whereby 479.8 g of the desired product (3, representing a yield of 99.4%) were obtained as a white powder.

A suspension of 12.04 g (50 mmoles) of the Mannich base (3) and 3 g of 10% Pd/C in 150 ml ethanol was hydrogenated at 60 psi for 17 hours at room temperature to produce 4. Without isolation of 4, acetic anhydride (10 ml) was added and the reaction mixture was filtered over a layer of Celite. Acetic anhydride (10.2 g, 100 mmole) and 4-dimethylaminopyridine (1 g) were added to the filtrate and the resultant mixture was stirred at 50° C. for 3 hours. The reaction mixture was poured over a 200 ml slurry of crushed ice and water to give 8.6 g (representing a yield of 86%) of the desired product (1). The overall yield of the process was 85.5%. Further investigation on larger quantities has shown that this procedure affords moderate yields ranging from 43–65%.

The Mannich reaction of 1-naphthol (2) with formaldehyde and various secondary amines, including piperidine, is known in the prior art. During the course of our work on the synthesis of 1-acetoxy-2-methylnaphthalene, the present inventors noted that the Mannich reaction of 1-naphthol produced a mixture of mono- and di- Mannich bases, with the former being predominant. Purification to give the pure mono-Mannich base is not an easy task. However, the present inventors found that when piperidine was employed, the mono-Mannich base (3) precipitated out of the reaction mixture. Possibly, precipitation of the product prevented the second Mannich reaction from occurring. The desired product was isolated by adding water and filtering off the resultant precipitate. The morpholinomethyl-1-naphthol described in the previously discussed 1975 Research Disclosure article was an oily material. Consequently, an extraction step was required. Dimethylamine, pyrrolidine and dibutylamine do not, however, yield satisfactory products. This has not been heretofore appreciated in the prior art. The process of Example 1 proved to be disadvantageous in that the reduction required high loading of Pd/C (greater than 20%); the acetylation had to be performed in the presence of an expensive organic base (such as 4-dimethylaminopyridine) and scale up of the synthesis did not provide consistent results.

As is evident from our earlier review of prior art processes, a number of methods are known for the production of 1-acetoxy-2-methylnaphthalene (1). However, they all suffer from one or more of the following disadvantages.

1. The overall yield of 1-acetoxy-2-methylnaphthalene is low.
2. Special conditions are required to carry out the reaction (e.g. high dilution or carrying out the reaction under a nitrogen blanket or in the dark).
3. The process requires isolation of 2-methyl-1-naphthol for further acetylation.
4. Expensive reagents, high catalyst loading (20% Pd/C) and purification steps are required.

The method of the present invention overcomes the aforementioned disadvantages of prior art processes. The process of the instant invention is a two step procedure carried out in one pot. Thus the process is very economical. In the two step process of the instant invention 2-piperidinomethyl-1-naphthol is convened into 2-acetoxymethyl-1-acetoxynaphthalene which, without isolation, is directly subjected to hydrogenation to produce 1-acetoxy-2-methylnaphthalene (1).

The process of the present invention for preparing 1-acetoxy-2-methyl-naphthalene (1) has several additional advantages over prior art methods. These advantages include:

1. The overall yield of 1-acetoxy-2-methylnaphthalene is very high.
2. No purification step is required.
3. The two-step process (acetylation and reduction) can be carried out in one pot, thus simplifying the entire operation.
4. Reduction time is decreased from 17 hours required for the piperidine Mannich base to 12 hours for the diacetoxy derivative.
5. No extraction step is required during the work up and 1-acetoxy-2-methylnaphthalene is isolated from water.
6. Inexpensive reagents and low catalyst loading (10% Pd/C) are employed.
7. Acetylation does not require an expensive base, such as 4-dimethylaminopyridine.

The process of the present invention for the synthesis of 1-acetoxy-2-methylnaphthalene (1) is illustrated by the following reaction scheme:

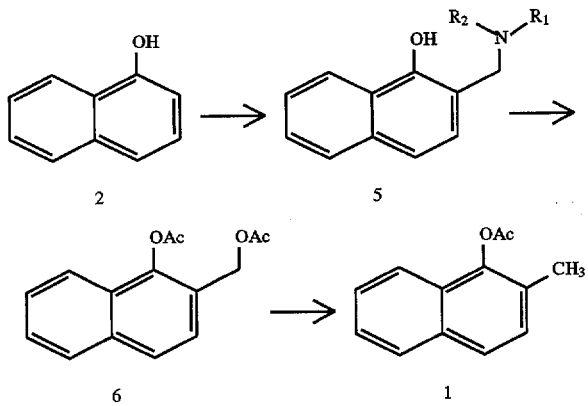

The Mannich reaction of 1-naphthol (2) with aqueous formaldehyde and a secondary amine $HNR_1R_2$ wherein $R_1$ and $R_2$ are independently selected from the group consisting of $C_1$–$C_{10}$ alkyl and benzyl, or $R_1$ and $R_2$ together with the nitrogen atom to which they are attached form piperidino, pyrrolo, morpholino, or a piperizino group, in a $C_1$–$C_6$ alkanol (such as methanol, ethanol and 2-propanol) or aqueous $C_1$–$C_6$ alkanol is carried out to produce the Mannich base (5). The Mannich base of Formula 5 is preferably prepared by reacting 1-naphthol (2) with a secondary amine selected from the group consisting of dimethylamine, diethylamine, depropylamine, dibutylamine, dipentylamine, dioctylamine, dibenzylamine, piperidine, pyrrole and morpholine.

Mannich base (5) is then convened into the diacetoxy derivative (6) by treatment with acetic anhydride. Catalytic hydrogenation or catalytic transfer hydrogenation of the diacetoxy derivative (6) affords 1-acetoxy-2-methylnaphthalene (1). When the reaction is complete, the catalyst is removed and the filtrate is taken up in ice water. The resulting precipitate is collected, washed with water and dried to afford 1-acetoxy-2-methylnaphthalene (1).

In the preferred mode of carrying out the process of the present invention, Mannich base (5) is piperidinomethyl-1-naphthol. The Mannich reaction is preferably carried out in 2-propanol or ethanol.

Examples 2 and 3, which follow, illustrate the preferred mode of carrying out the process of the present invention:

EXAMPLE 2

Piperidine (93.7 g, 1.1 moles) was added to a stirred solution of 144 g (1 mole) of 1-naphthol and 85 ml (1.1 moles) of 37% formaldehyde in 300 ml 2-propanol and 100 ml water, maintained in an ice/acetone bath. The piperidine addition was carried out over a period of 30 minutes. The reaction mixture was stirred for an additional 30 minutes. The resulting precipitate was filtered, washed 4 times with 75 ml portions of cold water, then dried to give 228.4 g (95% yield) of Mannich base (5) having a melting point of 137°–139° C. (133.5°–134.5° C., J. Org. Chem. 7, 31, 1942); $^1$HNMR (300 MHz, DMSO-$d_6$) δ 1.54 (m, 6H), 2.49 (bs, 4H), 3.81 (s, 2H), 7.13 (d, 1H, J=8.4 Hz), 7.27 (d, 1H, J=8.4 Hz), 7.41 (m, 2H), 7.76 (m, 1H), 8.06 (m, 1H).

EXAMPLE 3

A mixture of 60.30 g (25 mmoles) of Mannich base (5) and 63.8 g (625 mmoles) acetic anhydride was stirred at 70° C. for 12 hours to produce diacetoxy derivative (6). Ethanol (150 ml) was added to this mixture followed by the addition of 6.5 g of 10% Pd/C. The resultant mixture was hydrogenated at 60 psi hydrogen pressure for 12 hours then filtered over a layer of Celite. The filtrate was poured onto ice/water. The resulting off-white precipitate was collected, washed with water and dried to give 45.9 g (92% yield) of 1-acetoxy-2-methylnaphthalene (1) having a melting point of 81-82 ° C.; HNMR (300 MHz, acetone-$d_0$1.02 (s, 3H), 1.18 (s, 3H), 6.07 (d, 1H, J=8.4 Hz), 6.19 (m, 2 6.40 (d, 1H, J=8.1 Hz), 6.50 (d, 1H, J=7.8 Hz), 6.56 (d, 1H, J=8.1 Hz); MS m/z 200 (M+).

What is claimed is:

1. Process for producing 1-acetoxy-2-methylnaphthalene comprising the steps of:

(a) reacting acetic anhydride with a Mannich base of the formula 5,

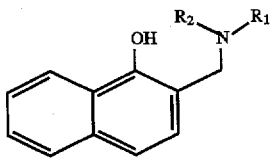

wherein $R_1$ and $R_2$ are independently selected from the group consisting of $C_1$–$C_{10}$ alkyl and benzyl, or $R_1$ and $R_2$ together with the nitrogen atom to which they are attached form piperidino, pyrrolo, morpholino, or a piperizino group, to produce a diacetoxyderivative of the Mannich base;

(b) hydrogenating the diacetoxy derivative by catalytic hydrogenation or catalytic transfer hydrogenation to produce a reaction mixture containing the 1-acetoxy-2-methyl-naphthalene.

2. The process according to claim 1, wherein steps (a) and (b) are carried out in one pot.

3. The process according to claim 1, further including the step of filtering catalyst from the reaction mixture to produce a filtrate; then mixing the filtrate with water to precipitate the 1-acetoxy-2-methyl naphthalene from the reaction mixture.

4. The process according to claim 1, wherein 10% Pd/C is employed as a catalyst in step (b).

5. The process according to claim 1, wherein the reaction of step (b) is carried out in $C_1$–$C_6$ alkanol.

6. The process according to claim 5, wherein the $C_1$–$C_6$ alkanol is 2-propanol.

7. The process according to claim 5, wherein the $C_1$–$C_6$ alkanol is ethanol.

8. The process according to claim 1, wherein the Mannich base of formula 5 is prepared by reacting 1-naphthol with a secondary amine selected from the group consisting of dimethylamine, diethylamine, dipropylamine, dibutylamine, dioctylamine, dibenzylamine, piperidine, pyrrole and morpholine.

* * * * *